(12) United States Patent
Spallek et al.

(10) Patent No.: US 10,238,813 B2
(45) Date of Patent: Mar. 26, 2019

(54) DISPENSING DEVICE WITH CONTROL BODY IN ORDER TO AXIALLY MOVE A DISPENSING ELEMENT

(71) Applicant: KOCHER-PLASTIK MASCHINENBAU GMBH, Sulzbach-Laufen (DE)

(72) Inventors: Michael Spallek, Ingelheim (DE); Johannes Geser, Gerlingen (DE); Alexander Hammer, Gaildorf (DE); Alexander Beier, Oberrot (DE); Alexander Muff, Buttisholz (CH)

(73) Assignee: KOCHER-PLASTIK MASCHINENBAU GMBH, Sulzbach-Laufen (DE)

( * ) Notice: Subject to any disclaimer, the term of this patent is extended or adjusted under 35 U.S.C. 154(b) by 49 days.

(21) Appl. No.: 15/311,984

(22) PCT Filed: May 12, 2015

(86) PCT No.: PCT/EP2015/000976
§ 371 (c)(1),
(2) Date: Nov. 17, 2016

(87) PCT Pub. No.: WO2015/185181
PCT Pub. Date: Dec. 10, 2015

(65) Prior Publication Data
US 2017/0128676 A1    May 11, 2017

(30) Foreign Application Priority Data
Jun. 6, 2014   (DE) .................. 10 2014 008 610

(51) Int. Cl.
*A61J 1/06*    (2006.01)
*A61M 5/24*   (2006.01)
(Continued)

(52) U.S. Cl.
CPC .......... *A61M 5/347* (2013.01); *A61M 5/2466* (2013.01); *A61M 5/282* (2013.01);
(Continued)

(58) Field of Classification Search
CPC .... A61M 5/2466; A61M 5/282; A61M 5/288; A61M 5/3202; A61M 5/347;
(Continued)

(56) References Cited

U.S. PATENT DOCUMENTS 6,090,093 A    7/2000  Thibault et al.
6,209,738 B1   4/2001  Jansen et al.
(Continued)

FOREIGN PATENT DOCUMENTS

| EP | 1 093 784 | 4/2001 |
|----|-----------|--------|
| WO | 03/057289 | 7/2003 |
| WO | 2012/113008 | 8/2012 |

OTHER PUBLICATIONS

International Search Report (ISR) dated Aug. 5, 2015 in International (PCT) Application No. PCT/EP2015/000976.

*Primary Examiner* — Nathan R Price
*Assistant Examiner* — Dung T Ulsh
(74) *Attorney, Agent, or Firm* — Wenderoth, Lind & Ponack, L.L.P.

(57) ABSTRACT

A dispensing device includes a container with a receiving space containing a dispensable medium extractable via a dispensing element. A control body (19) with a connecting body (11) is longitudinally displaceable in a housing part (9), from an inactive base position to an active extraction position by a rotational movement. A media-carrying connection is created between the receiving space and the dispensing element. A control part of the control body (19) can be attached to a control path (54) of the connecting body (11). When the control body (19) moves rotationally relative to (Continued)

the housing part (9), each control part follows the rotational movement in an axially unchanged manner and brings the connecting body from the base position to an extraction position via each associable control path (54) of the connecting body (11). The control path comprises a slope.

14 Claims, 12 Drawing Sheets

(51) Int. Cl.
| | |
|---|---|
| *A61M 5/28* | (2006.01) |
| *A61M 5/31* | (2006.01) |
| *A61M 5/32* | (2006.01) |
| *A61M 5/34* | (2006.01) |
| *A61M 5/50* | (2006.01) |
| *A61M 35/00* | (2006.01) |

(52) U.S. Cl.
CPC .......... *A61M 5/288* (2013.01); *A61M 5/3202* (2013.01); *A61M 35/003* (2013.01); *A61J 1/067* (2013.01); *A61M 5/5086* (2013.01); *A61M 2005/2474* (2013.01); *A61M 2005/312* (2013.01); *A61M 2005/3139* (2013.01)

(58) Field of Classification Search
CPC ........ A61M 5/5086; A61M 2005/2474; A61M 2005/312; A61M 2005/3139; A61M 35/003; A61J 1/067; A61J 1/20; A61J 1/2096; A61J 1/06
See application file for complete search history.

(56) References Cited

U.S. PATENT DOCUMENTS

| | | | |
|---|---|---|---|
| 2001/0003996 A1* | 6/2001 | Jansen | A61J 1/1406 |
| | | | 141/329 |
| 2004/0181190 A1* | 9/2004 | Hsu | A61M 5/322 |
| | | | 604/240 |
| 2007/0060885 A1* | 3/2007 | Wu | A61M 5/322 |
| | | | 604/110 |
| 2014/0052071 A1 | 2/2014 | Pickhard et al. | |

\* cited by examiner

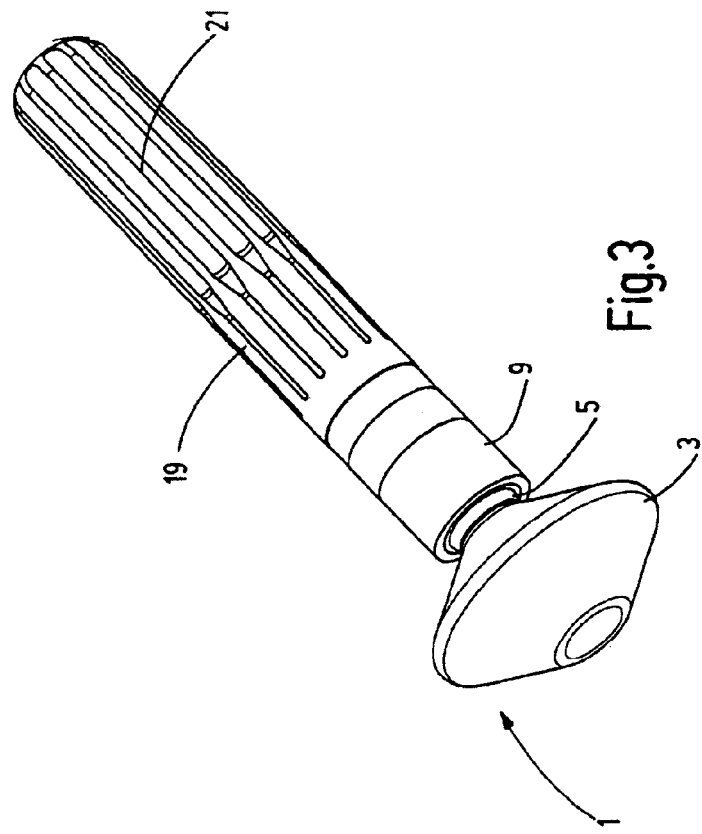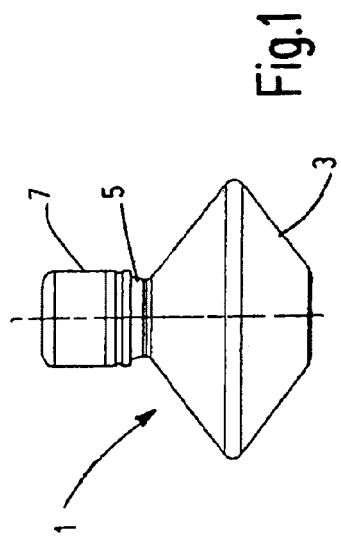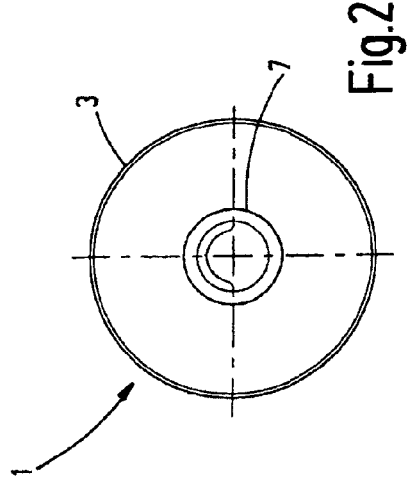

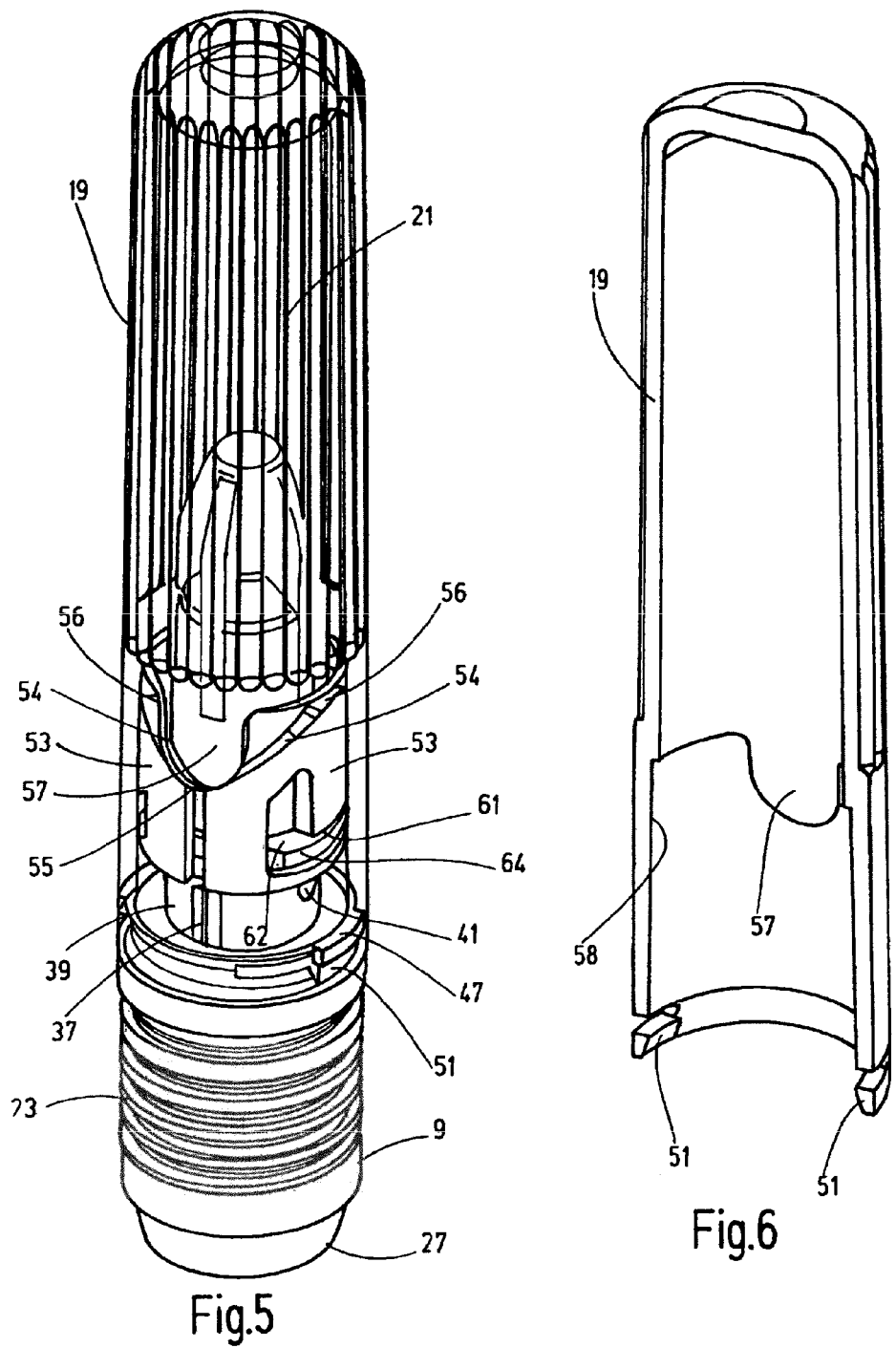

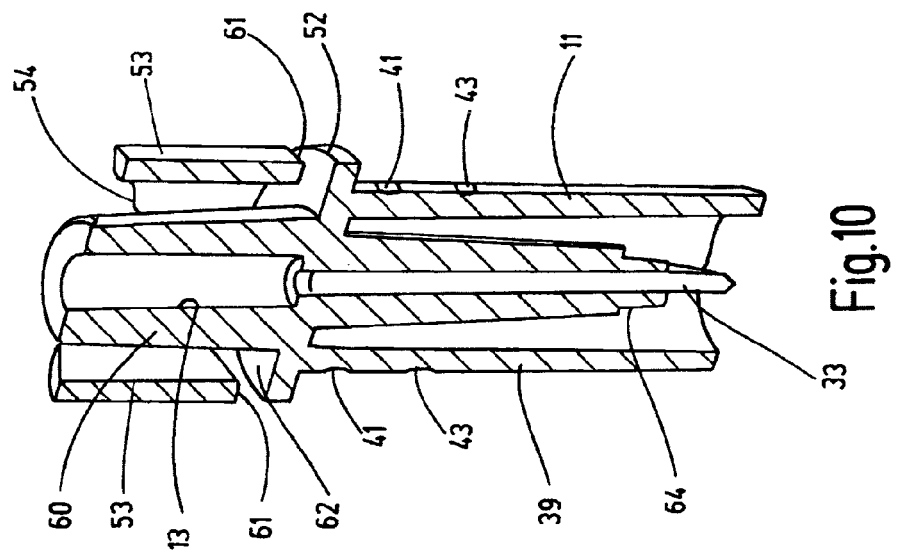
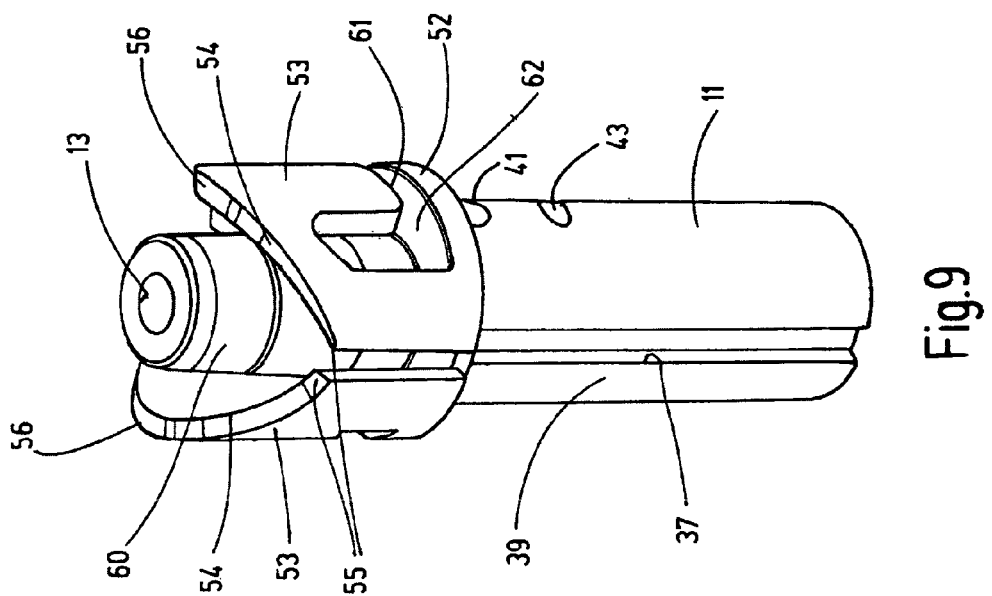

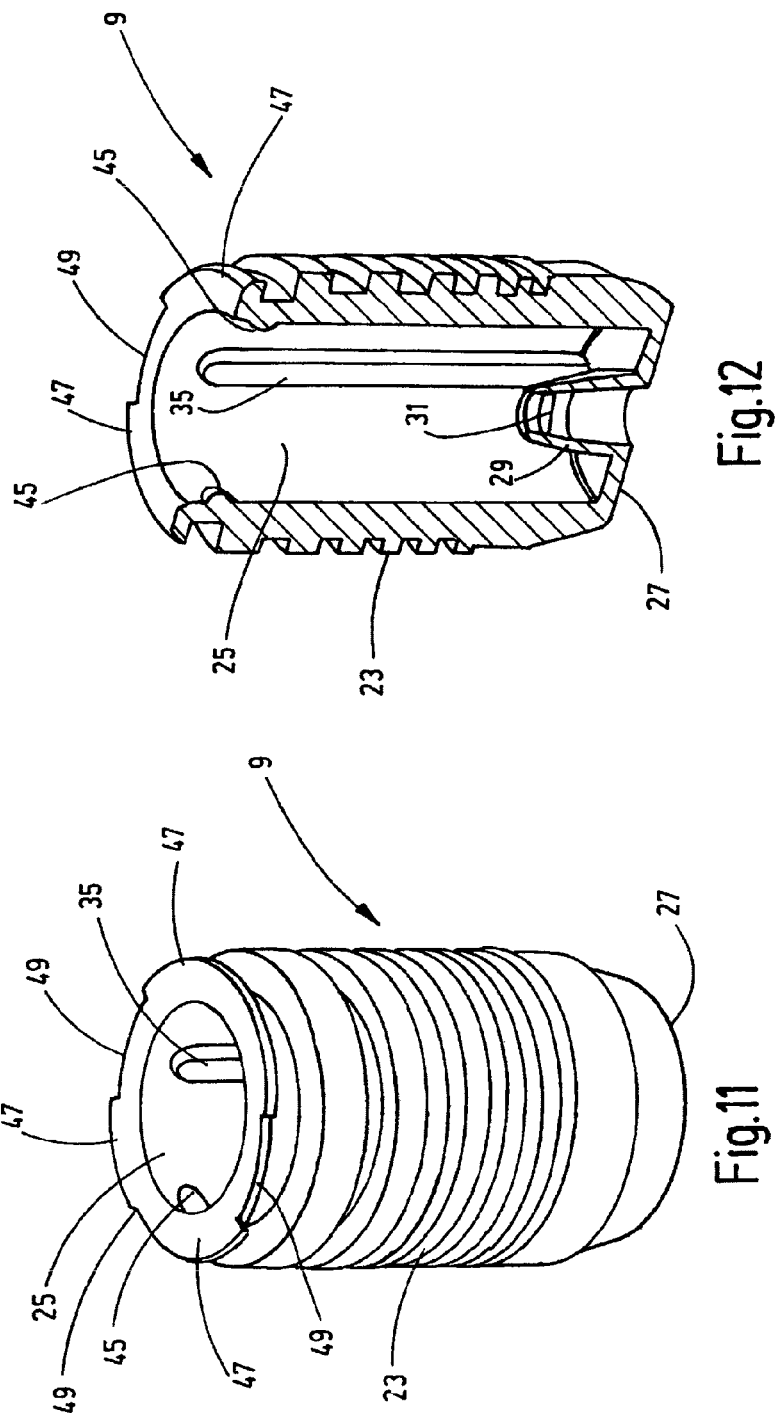

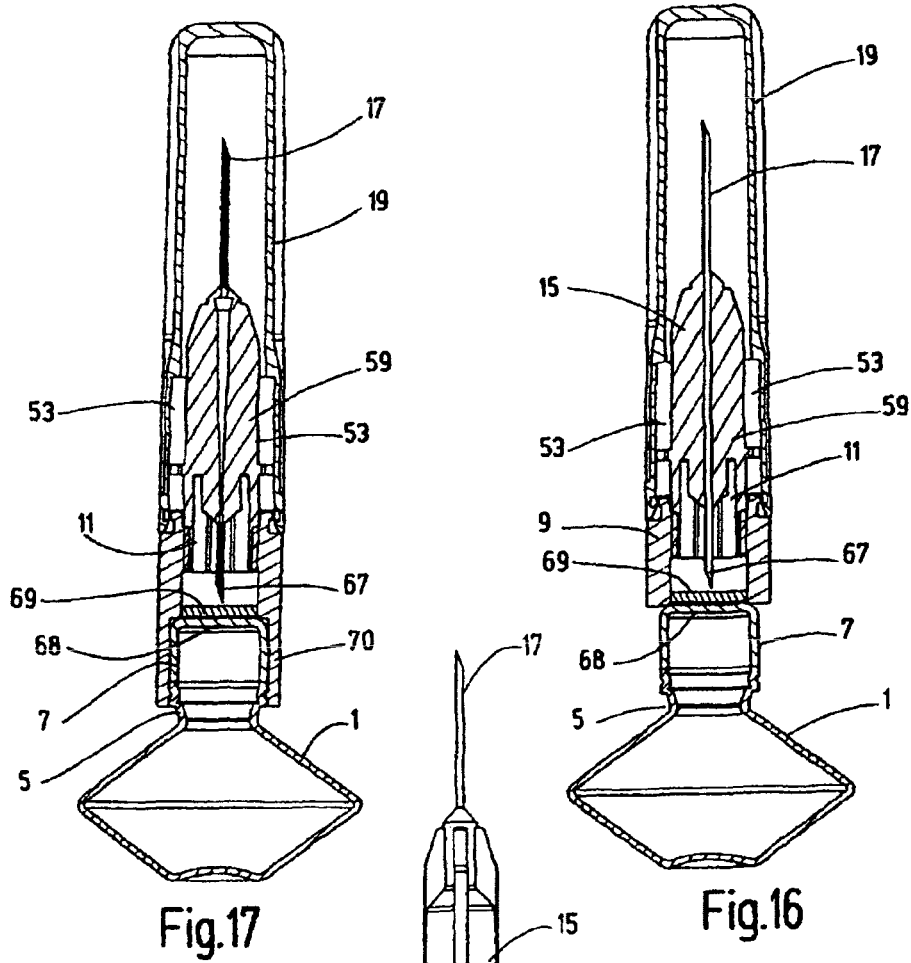
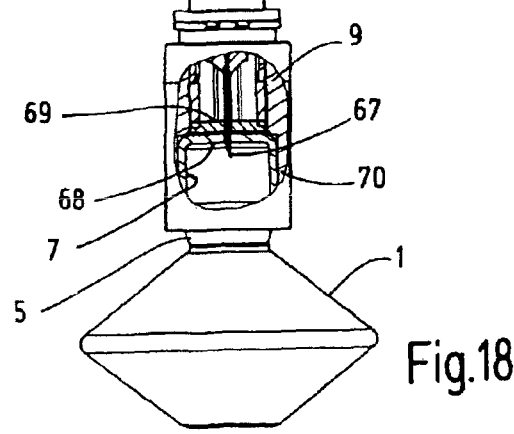

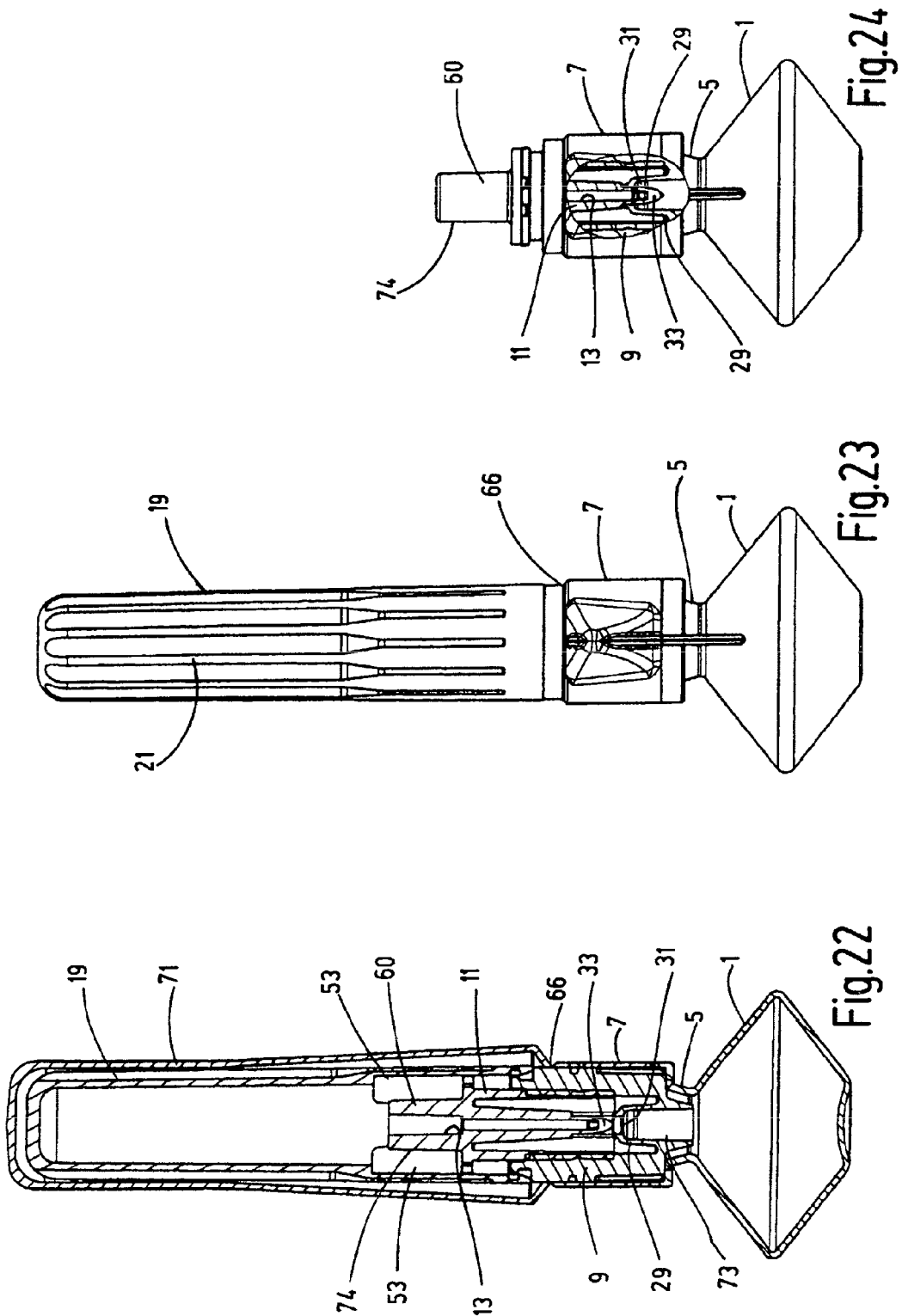

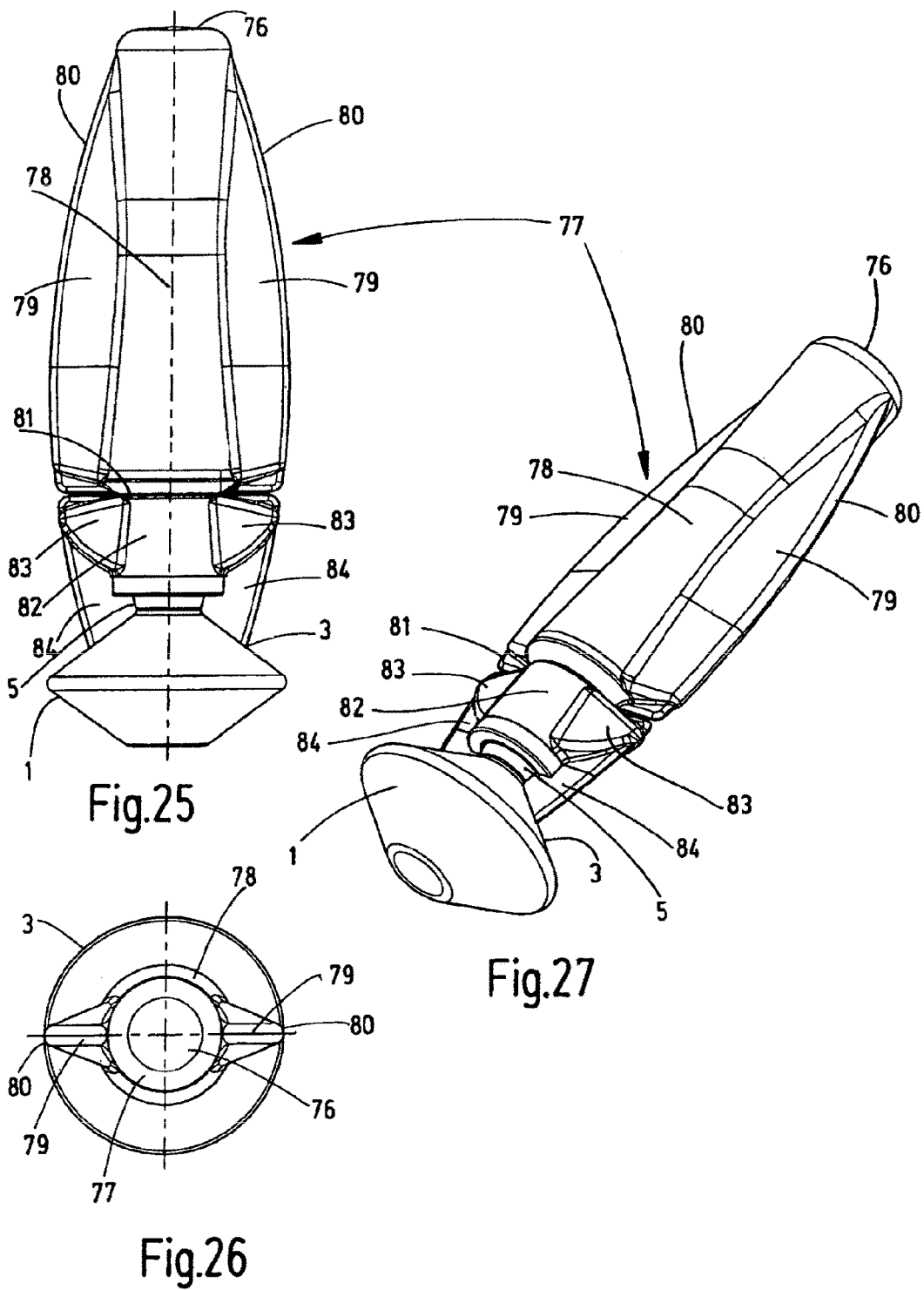

DISPENSING DEVICE WITH CONTROL BODY IN ORDER TO AXIALLY MOVE A DISPENSING ELEMENT

FIELD OF THE INVENTION

The invention relates to a dispensing device having the receiving space containing a dispensable medium that can be extracted by a dispensing element of the device for an extraction process, and having a control body that moves a connecting body, guided in a longitudinally displaceable manner in a housing part, from an inactive initial position to an active extraction position by a rotary motion. A media-carrying connection is created between the receiving space and the dispensing element. At least one control part of the control body can be brought into abutment with at least one control path of the connecting body.

BACKGROUND OF THE INVENTION

Dispensing devices of this type are used for technical, cosmetic, pharmaceutical and medical purposes, in particular in conjunction with injections for administering medication. The dispensing devices are intended to allow the operator to safely and conveniently perform the measures to be taken for the application of the container media, allowing, for instance in the case of disposable syringes, the delivery device to be used by the patient himself. As prior art, WO 2012/113008 discloses a dispensing device of the type initially referred to, in the form of a syringe head for an injection syringe. A protective cover for the injection needle forming the dispensing orifice is provided as a control body to be operated for an extraction process. By a rotary movement of the protective cover, a connecting body bearing the injection needle is axially movable in a housing part. The housing part can be coupled to an injection cylinder in such a way that the connecting body establishes a media connection with the container, here the interior of the injection cylinder. In order to convert the rotary movement of the protective cover into the axial movement of the connecting body, in the known solution a drive part, which is connected in rotation to the protective cover and is referred to in the document as a "pinion", has circumferential, radially projecting guide knobs. The guide knobs are arranged in the housing part that is mounted on the container, in this case on the injection cylinder. Depending on the inclination of the slotted-guide tracks, the rotational movement transmitted by coupler lamellae from the protective cover to the pinion causes the longitudinal displacement of the pinion and through this displacement the opening movement of the connecting body.

The known solution is unsatisfactory in several respects. On the one hand, the design of the coupling connection between the protective cover and the pinion entails a corresponding structural complexity. On the other hand, the reliability of the function leaves a lot to be desired, as, for the typically used polymer materials with limited stiffness, the entry of the guide knob into the slotted-guide tracks and the guidance inside the slotted-guide tracks are do not prevent jamming.

In addition, the pinion has to fit tightly over the cannula during manufacture, which can easily result in damage to the needle tip and/or to the silicone layer on the needle. That damage can directly affect the user, as such damage can easily lead to painful injections.

SUMMARY OF THE INVENTION

Based on this state of the art, the invention addresses the problem of providing a dispensing device of the type mentioned at the outset, which is characterized by an improved functional reliability in a simple design.

According to the invention, this problem is basically solved by a dispensing device having, as an essential feature of the invention, during the rotary movement of the control body, the respective control part follows the rotary movement relative to the housing part in an axially unchanged manner and, via the respective control path of the connecting body, which has a slope, moves the connecting body from the initial position to the extraction position. Because the arrangement is such that the control part does not execute an axial movement during the rotary actuation, no clutch device is required to permit an axial movement between the control element and the control part upon transmission of the actuating torque. The device according to the invention can be realized in a particularly fail-safe manner using a simplified design based on conventional plastic materials, such as polyolefins.

In particularly advantageous exemplary embodiments, the control body has two control parts that are diametrically opposite in relation to the longitudinal axis of the device. In the initial position of the connecting body, the control parts are rotatable from a lower vertex position formed by the respective control paths of the connecting body in the direction of an upper vertex position of the respective control paths. The control parts are arranged above the lower vertex position in the initial position of the connecting body in axial direction, relative to the longitudinal axis. Unlike WO 2012/113008, in which the axial displacement of the connecting body tightly enclosing the cannula is transmitted to the connecting body via an axially movable pinion, the connecting body can be directly actuated via the axially immobile control parts of the control body, which are supported by the control paths of the connecting body and which upon rotary movement move away from the lower vertex position of the guide paths and thereby effect the axial displacement of the connecting body in a particularly secure manner.

In a particularly advantageous manner, the respective control path can encompass, at least partially, in a hollow ring-shaped and co-axial manner, a connecting channel, which is located in the connecting body and which constitutes the media connection to the container. A functional body specifically designed for the particular container application is arranged on the connecting body. In this case, the functional body can, for instance in the case of an injection, have a cannula. In the case of a transfer into another receptacle, the closure of which has to be punctured, the functional body can have a hollow mandrel. In the case of a dropper application, the functional body can have a dropper. In the case of ointment or gel application, the functional body can have an ointment applicator. In the case of an as yet unknown application, the functional body can have a connecting element, for example a conical connection.

Functional bodies and connecting bodies can be separate components, which may, for instance, be interlockable. This arrangement has the advantage of using similar connecting bodies for different functional bodies. Alternatively, connecting bodies and functional bodies can also be integral with each other, i.e. no sealing is required between the connecting channel and the functional body.

The control body can be designed in the manner of a protective cover for the respective functional bodies, supporting on its inside the control part in the form of at least one inwardly projecting lug part. The lug part is formed at least partly convex in the direction of the connecting body when the protective cover is on.

For particularly advantageous exemplary embodiments, the protective cover can, in the direction of its open free end having at least one protruding annular segment, reach under an assignable annular segment of the housing part in the inactive initial position of the protective cover at this housing part. After a rotation of the protective cover around a predetermined distance, until the connecting body has reached its active extraction position, the paired annular segments, which are disengaged from one another, and the protective cover, can then be removed from the housing part. Whereas, in the case of the aforementioned WO 2012/113008, in which the protective cover is merely secured by way of a predetermined breaking point on the housing part, there is the risk of the operator removing the protective cover after partial rotational actuation by detachment of the predetermined breaking point, and thus, no effective extraction process can be carried out. This risk is eliminated in the invention because the protective cover can only be removed when the active extraction position has been reached.

With particular advantage, the connecting body is provided with at least one longitudinal guide, guided longitudinally movably in the housing part and secured against all rotational movement.

Depending on the application purpose of the device, the respective containers can be molded to the housing part and/or subsequently be connected to the housing part as an independent component. In a particularly advantageous manner, for a dispensing device allocated to a container, which is produced in a blow-molding process, such as the known Bottelpack® process and filled in the mold, the container can be connected to the housing part in the blow mold.

The subject matter of the invention is also a carrier unit for a functional body which is provided, in particular, for a dispensing device.

As a further subject matter, the invention provides a container system having an outer closed sheath, the sheath parts of which can be separated from each other along at least one separation point, to expose a dispensing device.

Other objects, advantages and salient features of the present invention will become apparent from the following detailed description, which, taken in conjunction with the drawings, discloses preferred embodiments of the present invention.

BRIEF DESCRIPTION OF THE DRAWINGS

Referring to the drawings that form a part of this disclosure:

FIGS. 1 and 2 are show a front view and an end plan view, respectively, of a filled plastic container, which can be compressed in the manner of a bellows for an extraction process, carried out by an extraction or dispensing device according to the invention;

FIG. 3 is a perspective view of the container of FIGS. 1 and 2 with an extraction or dispensing device according to a first exemplary embodiment of the invention;

FIG. 5 is a perspective view of the extraction device of FIG. 3, partly cut-away and partly translucent;

FIG. 6 is a perspective view in section of the protective cover of FIG. 3;

FIG. 9 is an enlarged perspective view of the connecting body of FIG. 3;

FIG. 10 is a perspective view in section the connecting body of FIG. 9;

FIG. 11 is a perspective view of the separately illustrated housing part of the extraction device of FIG. 3;

FIG. 12 is a perspective view in section of the housing part of FIG. 11;

FIGS. 16 and 17 are front view sections of dispensing devices according to third and fourth exemplary embodiments, respectively, of the invention;

FIG. 18 is a front view, partially cut away, of the dispensing device of FIG. 17 in the extraction position with the protective cover removed;

FIG. 22 is a front view in section of a dispensing device according to a sixth exemplary embodiment of the invention having an outer sheath;

FIG. 23 is a front view of the dispensing device of FIG. 22 without the outer sheath;

FIG. 24 is a partially cut-away, front view of the dispensing device of FIGS. 22 and 23, in the extraction position without the protective cover;

FIGS. 25 and 26 are a front view and a top view of a container system according to a seventh exemplary embodiment of the invention, comprising a container, a dispensing device and an outer sheath;

FIG. 27 is a perspective oblique view of the container system of FIGS. 25 and 25.

DETAILED DESCRIPTION OF THE INVENTION

Figure 4:
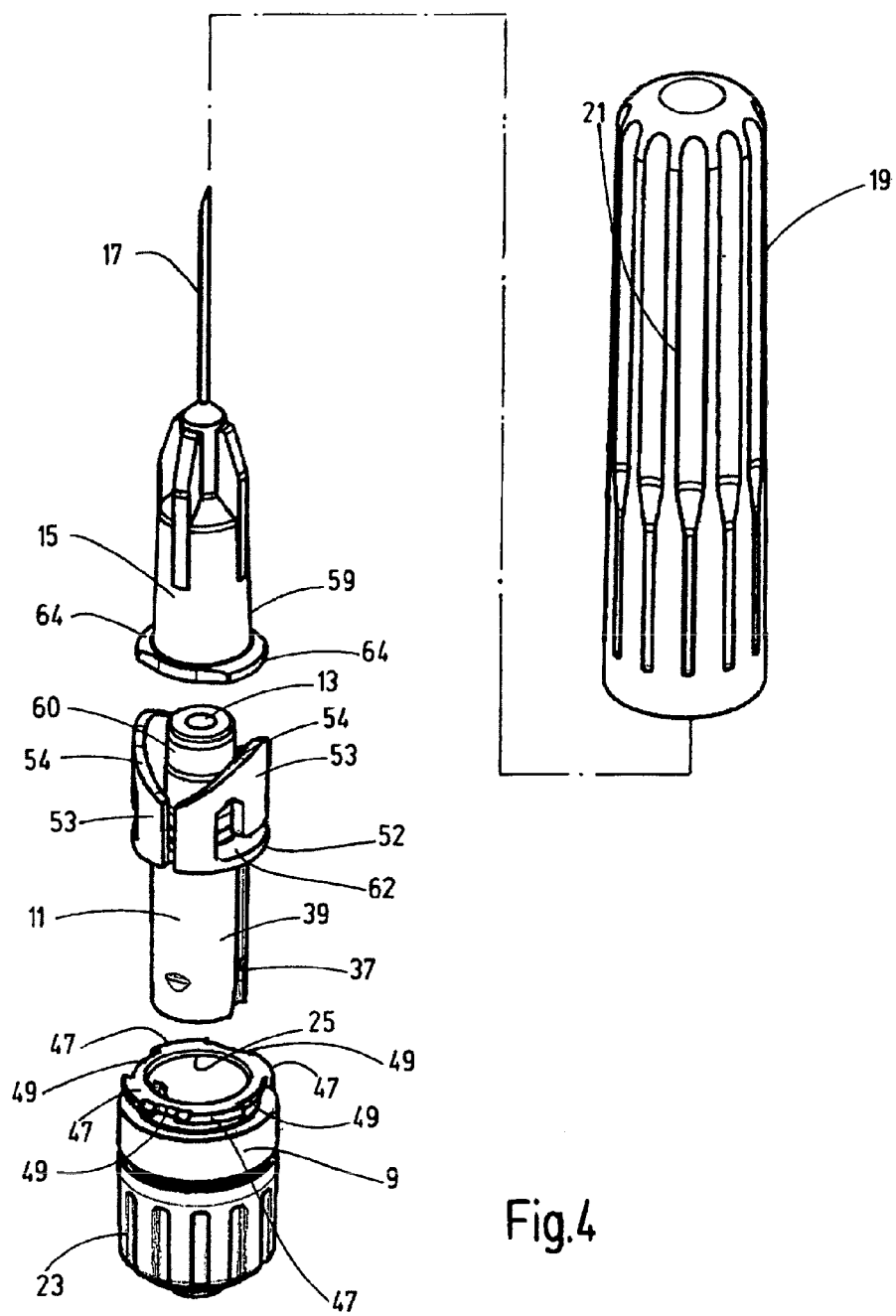
FIG. 4 is an exploded perspective view of the components of the extraction device of FIG. 3.

With reference to the drawings, the invention is explained by a number of examples, in which the dispensing device for the extraction of liquid or semi-solid filling material from a plastic container is provided. The plastic container can be in the form of an ampoule, for instance, made according to the Bottelpack® method, being manufactured and filled in a blow mold. FIGS. 1 and 2 show, in separate views, a corresponding container 1 having a container body 3, which is designed and is compressible in the manner of a flat bellows, so that it can be used for carrying out an application process, e.g. an injection process. The container 1 in the illustrated examples designed for a filling volume of 1 to 2 ml transitions from the container body 3 via a collar part 5 into a neck part 7. If that container 1 is provided for use in connection with an extraction or dispensing device according to the invention, the extraction or dispensing device is attached to the neck part 7 by a housing part 9, as shown in FIG. 3.

FIG. 4 shows the components of a first exemplary embodiment of the extraction or dispensing device according to the invention having a connecting body 11 guided such that it can move longitudinally in the housing part 9. Connecting body 11 has an inner, axial connection channel 13 for a fluid-conducting or fluid communication connection to the contents of the container 1 during the extraction or dispensing process. A functional body 15 adjoins the upper, in FIG. 4, end of the connecting body 11, and continues the inner channel 13 of the connecting body 11 to a functional part forming the dispensing element, in the present example, an injection needle 17. The upper termination of the device is formed by a protective cover 19, which in the mounted position, see FIGS. 5, 7 and 8, reaches over the functional body 15 and the connecting body 11. The open rim region of protective cover 19 is locked to the housing part 9, as will be explained in more detail below. The protective cover 19 forms a control body, which can be used to transfer the device from the initial position into an active extraction position. This transfer happens by a rotary movement of the protective cover 19, which is provided with an external longitudinal corrugation 21 for good traction.

Figure 13:
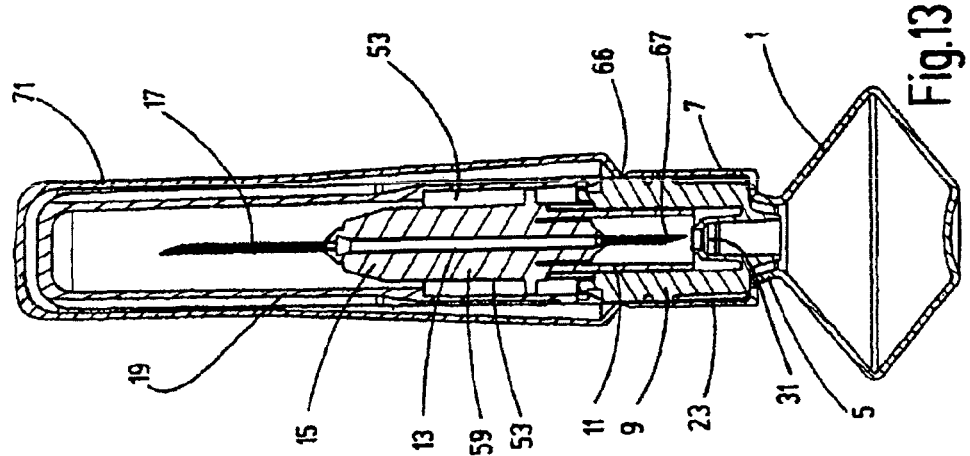
FIG. 13 is a front view in section of a dispensing device, provided with an outer sheath surrounding the protective cover according to a second exemplary embodiment of the invention.

Further details of the construction of the housing part 9 and the connecting body 11 can be seen more clearly in FIGS. 9 to 12. The housing part 9 has, on the whole, the shape of a hollow cylinder having a coaxial inner cavity 25, which is closed at the end 27 located at the bottom in FIGS. 11 and 12. If the extraction device, as in the case of the present exemplary embodiment, is provided for the extraction of filling material from a container 1, which is produced in a blow molding process and is filled in the mold, the complete assembly shown in FIG. 5 can be inserted into the extraction device as an insert before the final closure of the blow mold. When the head jaws of the mold are closed, the plastic hose forming the neck part 7 of the container 1 is then molded to the outside of the housing part 9, as can be seen in FIG. 13. The closed end 27 of the housing part 9 thus forms the container closure. A circumferential ribbing 23 on the housing part 9, which is shown as a longitudinal ribbing in FIG. 4 and a horizontal ribbing in FIGS. 11 and 12, forms a kind of gearing for a fixation based on a positive-locking engagement during the shaping of the neck part 7.

From the closed end 27, a truncated cone 29, open at the inner end thereof, extends coaxially into the cavity 25. Close to its opening, the truncated cone 29 is closed by a membrane 31, forming the perforation region. Membrane 31 is pierced in the extraction process, see FIGS. 7 and 8, by a hollow mandrel 33. Membrane 33 as shown most clearly in FIG. 10, forms the lower end of the connecting channel 13 in the connecting body 11. The connecting body 11 is displaceable in the cavity 25 of the housing part 9 for moving it from the initial position (FIG. 7) into the extraction position (FIG. 8), in which the mandrel 33 has pierced the membrane 31. Longitudinal ribs 35 on the housing part 9 form a longitudinal guide in conjunction with longitudinal grooves 37 in the cylinder jacket 39 of the connecting body 11. For an engagement of the connecting part 11 in the initial position and in the axial positions corresponding to the extraction position, upper latching notches 41 and lower latching notches 43 are formed at respectively diametrically opposed locations on the cylinder jacket 39 of the connecting body 11, for engagement with latching lugs 45 on the inside of the cavity 25 of the housing part 9 in the initial position or in the extraction position.

As mentioned before, the protective cover 19 is locked on the housing part 9 at the rotational position corresponding to the initial position. For this purpose, it has annular segments 47 at the open end, between which gaps 49 are located. As complementary locking elements, projecting annular segments 51 are formed at the open end of the protective cover 19, which reach under the annular segments 47 on the housing part 9 at the rotational position corresponding to the initial position, as shown in FIG. 5. When the protective cover 19 is rotated into the rotational position corresponding to the extraction position, annular segments 51 in the region of the gaps 49 are removed from the engagement with the annular segments 47 and the protective cover 19 can be removed. In that way, a bayonet-type interlock is formed.

Figures 7, 8:
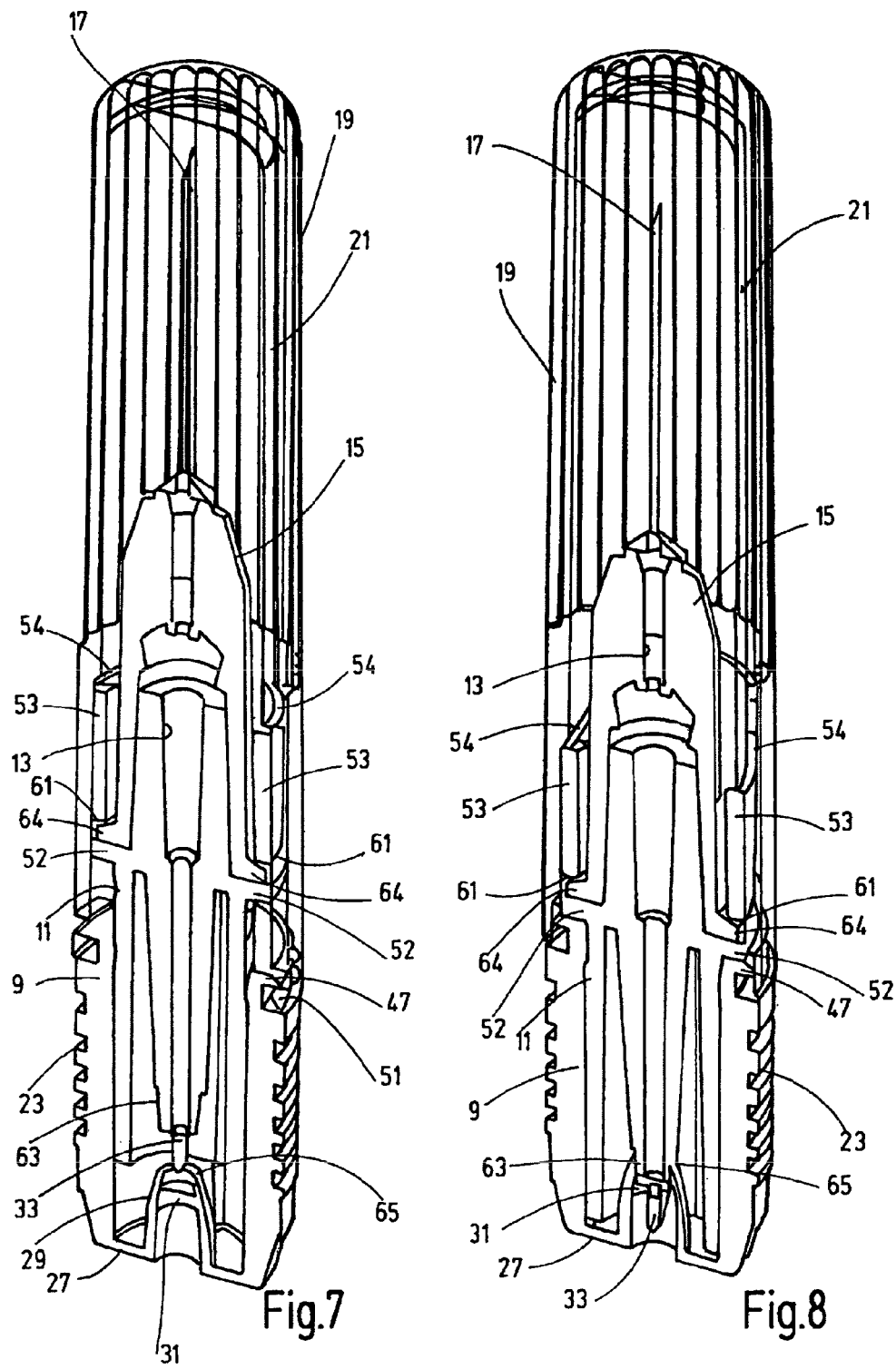
FIGS. 7 and 8 are perspective views in section of the extraction device of FIG. 3 being shown in the initial position (FIG. 7) and the extraction position (FIG. 8), respectively.

As can best seen in FIGS. 9 and 10, the connecting body 11 has a radially protruding flange part 52 at the upper end of its cylinder jacket 39. The wall parts 53 of connecting body 11 form parts of a circular cylinder and extend coaxially. The free upper rim of the wall parts 53 forms control paths 54, which extend between the lower vertex position 55 and the upper vertex position 56. Each control path has first and second sloped sections that are mirror images of one another as shown in FIG. 9. To generate the longitudinal displacement of the connecting body 11 from the initial position into the extraction position, the protective cover 19 has two control parts, which are diametrically opposite in relation to the longitudinal axis of the device. As can best be seen in FIGS. 5 and 6, they have the shape of lugs 57 that are rounded at their ends. Lugs 57 are arranged in the interior of the protective cover 19 at the transition to a radially expanded cylinder section 58 of the protective cover 19. Cylinder section 58 is arranged on the outside of the wall parts 53 of the connecting body 11. FIGS. 5 and 7 show the rotational position of the initial position, in which the ends of the lugs 57 are located at the lower vertex position 55 of the control paths 54. If the protective cover 19 is rotated by 90° in one or the other direction of rotation, the lugs 57 move towards the upper vertex position 56 of the control paths 54, generating the axial displacement of the connecting body 11, and thus, the movement of the mandrel 33 piercing through the membrane 31, at unchanged axial positions of the protective cover 19 and the housing part 9. For a pierced membrane 31 (FIG. 8), the part of the connecting body 11 surrounding the channel 13 and forming the mandrel 33, extends into the truncated cone 29 with an end cone 63. The end rim 65 of cone 29 is then in contact with the end cone 63 as a sealing lip. If the protective cover 19 reaches the position rotated by 90° and if the extraction position is reached, the annular segments 51 of the protective cover 19 come into alignment with the gaps 49 on the housing part 9 allowing the protective cover 19 to be removed. The injection needle 17 is then released for an application procedure.

As can be seen most clearly in FIG. 4, the functional body 15 as carrier of the injection needle has an initial body 59 which, as can be seen most clearly from FIGS. 7 and 8, reaches over a pin part 60. At the connecting body 11, pin part 60 surrounds the end section of the connecting channel 13. The fluid connection from the connecting channel 13 to the needle 17 continues in the interior of the initial body 59. The functional body 15 has, for attachment to the connecting body 11, flange parts 64 radially projecting from the lower edge region. In the installed state flange parts 64 adjoin the planar upper side 62 of the flange parts 52 of the connecting body 11 and are held thereon by wall parts 61. Wall parts 61 are formed on cutouts of the wall parts 53 of the connecting body 11. By the functional body 15 thus fixed to the extraction device, the protective cover 19 can be removed in the extraction position. An extraction process can then be carried out by executing an application of filling material by the injection needle 17 by compressing the bellows-shaped container body 3 of the container 1. The same applies to the application of drops, e.g. for oral, nasal, ophthalmic, topical, etc. treatments, as well as the application of semi-solid products such as ointments, creams or gels, using suitable, applicators known per se.

Figure 15:
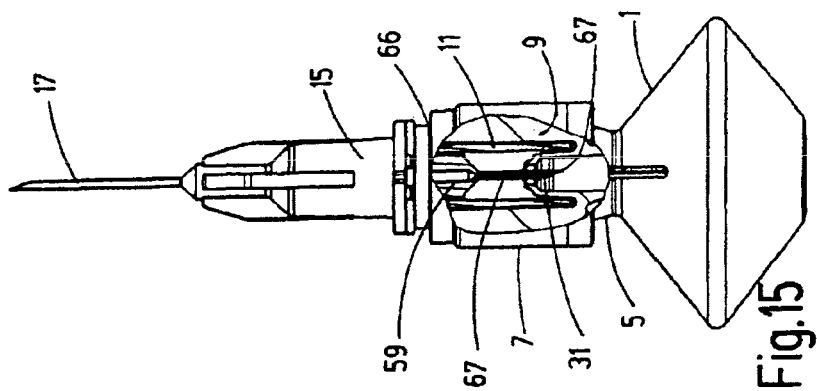
FIG. 15 is a front view, partially cut away, of the dispensing device of FIGS. 13 and 14, in the extraction position with the protective cover removed.
Figure 14:
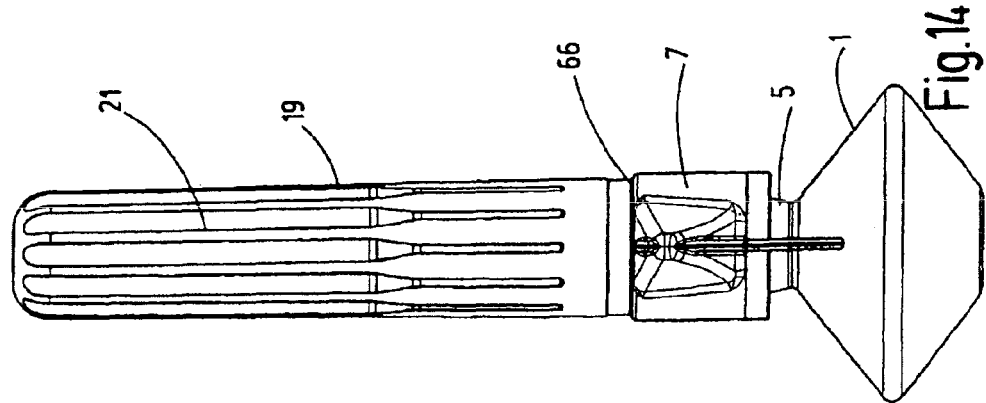
FIG. 14 is a front view of the dispensing device of FIG. 13, with the sheath removed.

FIGS. 13 to 15 show a modified second exemplary embodiment in which the protective cover 19 is enclosed by an outer sheath 71. This outer sheath can be formed during the production of the container 1 by blow molding from the plastic hose adjoining the neck part 7, which hose is extruded into the blow mold, when the mold head jaws are closed. A predetermined breaking point 66 (FIG. 13) can be formed at the place of attachment to the neck part 7, where the sheath 71 can be detached together with the protective cover 19. As a further difference to the previous exemplary embodiment, the connecting body 11 does not have a mandrel 33 made of plastic molded onto the main body 59, but a hollow needle 67, which is shown in the initial position in FIG. 13 and in the extraction position after piercing the membrane 31 in FIG. 15. In this embodiment, the part of the connecting body 11 is eliminated, which in the previously described exemplary embodiment forms the end cone 63 having the adjoining mandrel 33 at the end of the connecting channel 13, as the hollow needle 67 itself forms the seal on the pierced membrane 31.

In a preferred case (not shown), the needle 17 and the hollow needle 67 may be formed integrally, as a double-pointed injection needle, resulting in a small, unusable dead volume.

FIG. 16 shows an exemplary embodiment in which, as in the example of FIGS. 13 to 15, a hollow needle 67 is provided on the base body 59 of the functional body 15, instead of a plastic mandrel 33 molded to the connecting part 11. In the example of FIG. 16, however, the container 1 is not molded with its neck part 7 to the outside of the housing part 9. On the contrary, the container 1 has a closed neck part 7, to which the housing part 9 is tightly connected, e.g. glued, locked or welded. As shown in FIG. 16, a sealing layer 69 made of an elastomer rests on the planar upper end wall 68. In the extraction position, the hollow needle 67 penetrates the elastomer material and the wall 68 of the neck part 7.

The further exemplary embodiment shown in FIGS. 17 and 18 differs from the example of FIG. 16 only in that the housing part 9 has a sleeve-shaped extension 70, which is used to snap the housing part 9 onto the outside of the neck part 7 of the container 1. Again, the neck part 7 is closed by a planar wall 68, to which a sealing layer 69 of elastomer is attached. FIG. 18 shows the extraction state having a pierced sealing layer 69 and pierced wall 68.

Figure 21:
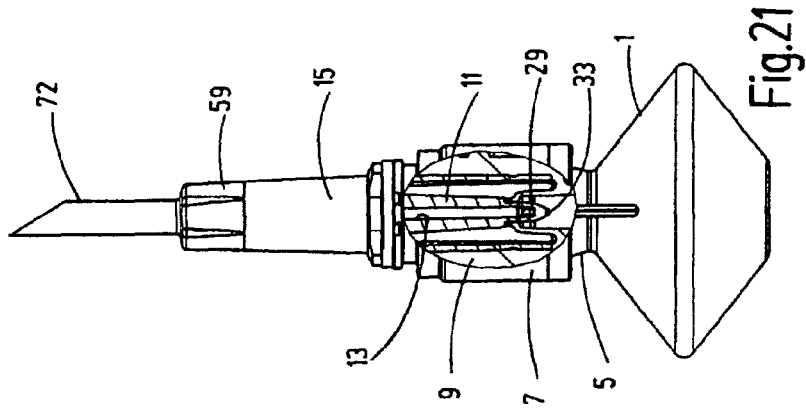
FIG. 21 is a partially cut-away front view of the dispensing device of FIGS. 19 and 20, shown in the extraction position.
Figure 20:
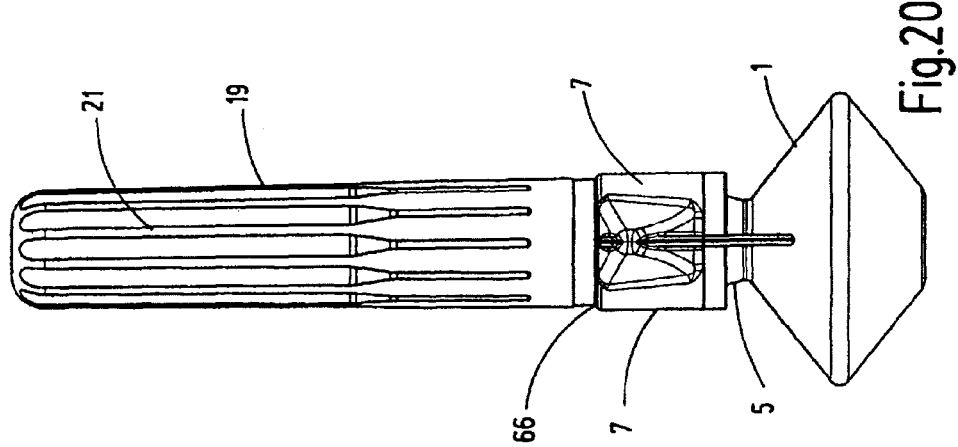
FIG. 20 is a front view of the dispensing device of FIG. 19 with the outer sheath removed.
Figure 19:
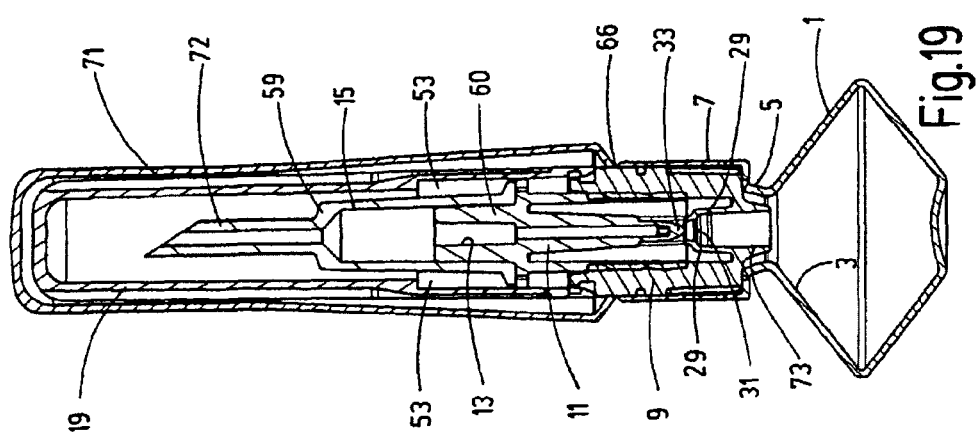
FIG. 19 is a front view in section of a dispensing device according to a fifth exemplary embodiment of the invention, having an outer sheath attached thereon.

In the further exemplary embodiment of FIGS. 19 to 21, the neck part 7 of the container 1 is again molded onto the outer side of the housing part 9, as in the examples of FIGS. 1 to 15. Also, a plastic mandrel 33 is formed onto the connecting body 11 for piercing the diaphragm 31 of the housing part 9. Instead of an injection needle 17 forming the dispensing element, a hollow application pin 72 is mounted to the base body 59 of the functional body 15. By mandrel 72, for instance, an elastomer closure of an injection bottle or an infusion bag can be pierced. As a further difference to the first-described embodiment of the housing part 9 in the example of FIGS. 19 to 21, the housing part 9 has a hollow end cone 73 extending along the inside of the collar part 5 into the inside of the container body 3 at the end facing the container 1. Furthermore, as in the example of FIGS. 13 to 15, an outer sheath 71 surrounding the protective cover 19 is detachably molded over a predetermined breaking point 66.

The further modified exemplary embodiment of FIGS. 22 to 24 corresponds to the exemplary embodiment of FIGS. 19 to 21, with the difference that no functional body 15 continuing the connection channel 13 is attached to the connecting body 11. Rather, the end-side pin part 60 of the connecting body 11 is designed as a connection part, for instance in the form of a conical connection 74 or for the formation of an interlockable conical connection part. As provided in the examples of FIGS. 13 and 19, an outer sheath 71 is provided for the protective cover 19. The outer sheath 71 former can be removed together with the protective cover 19 after the predetermined breaking point 66 has been released. Particularly advantageous is a substance-to-substance, positive-locking and/or form-locked connection of protective cover 19 and outer sheath 71.

FIGS. 25 to 28 show an exemplary embodiment in which the dispensing device forms a completely encapsulated container system. In this regard, several casing parts are provided, which extend from the container body 3 of the container 1 to the upper end 76 allocated to the dispensing element. In this case, a first casing part 77 is provided, which conjunctively surrounds, starting at the upper end 76, the inner protective cover 19 with a central part 78 having the form of an externally concave, curved tubular body with laterally projecting wing parts 79 arranged diametrically opposite to each other as handle parts. The wing parts 79 have a convexly curved end rim 80. This casing part 77 is detachably connected to a second casing part 82, which surrounds the housing part 9, via a predetermined break point 81. Wing-shaped grip flaps 83, which are aligned with the wing parts 79 of the first casing part 77, extend diametrically outwards from the second casing part 82. Stay bars 84 extend from the grip straps 83 to the outside of the container body 3.

The casing part 77 is connected to the outer longitudinal corrugation 21 of the protective cover 19. In this way, by releasing the predetermined breaking point by rotating into any direction of rotation, the rotary movement of the protective cover 19 is simultaneously initiated to move the device into the extraction position, where the protective cover 19 can be removed. The first casing part 77 can be conveniently separated by the wing parts 79 serving as handles. When the device is in the extraction position, i.e. after removal of the casing part 77 together with the protective cover 19, the device can be conveniently handled for the respective intended application processes by the lateral grip straps 83 remaining in connection with the container body 3. In the case of the bracing formed by the bars 84, the functional body 15 can be safely used, for instance, for injection purposes, without the premature compression of the container body 3 occurring, because the actuating force for activating the dispensing device is not applied via the container 3 but via the grip straps 83.

Figure 28:
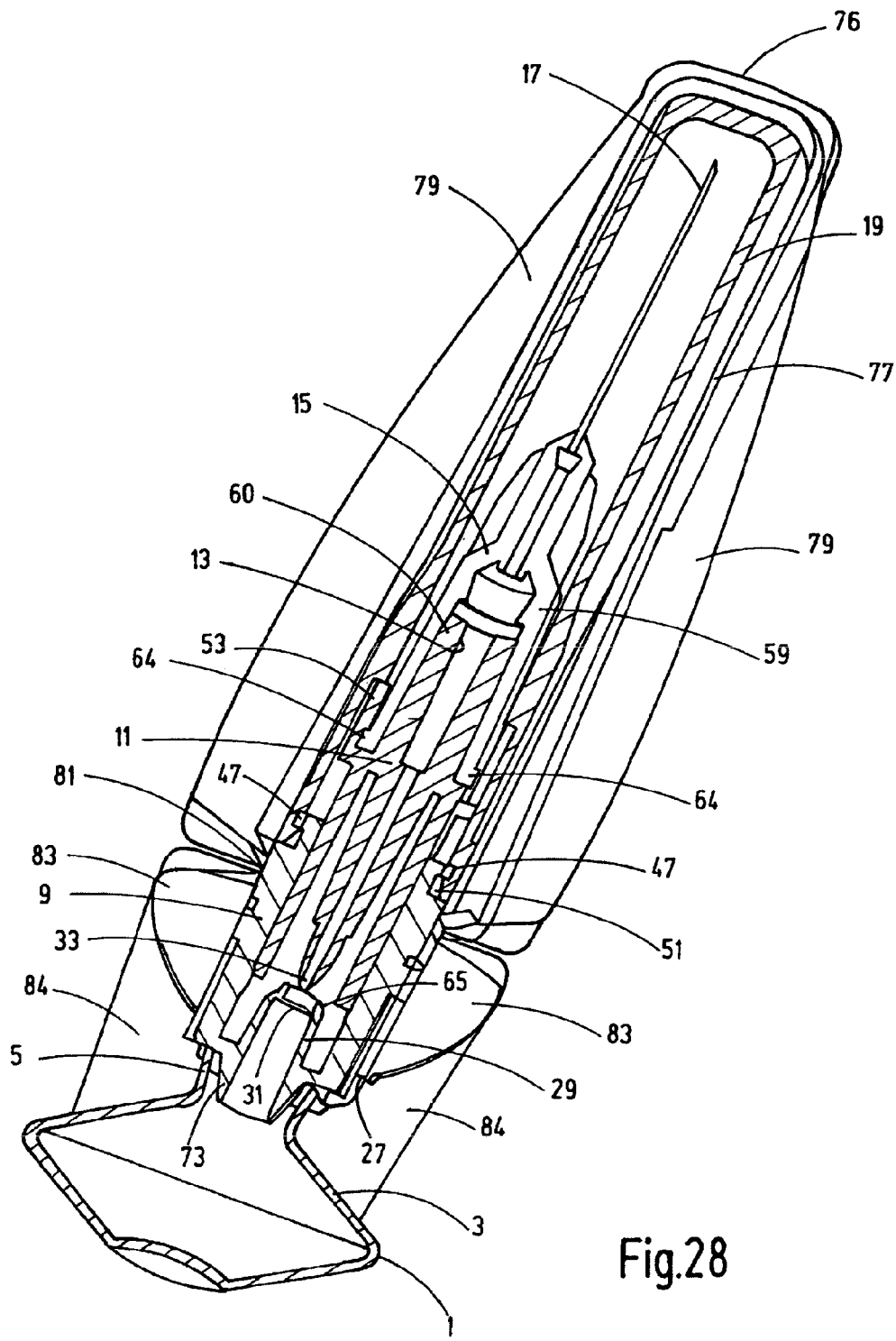
FIG. 28 is a cut-away perspective view of the container system of FIGS. 25 to 27 in a larger scale.

The internal structure of the device, not shown in FIGS. 25 to 27, can essentially correspond to the exemplary embodiment described first, as illustrated by way of example in FIG. 28. It goes without saying that variations of averted device parts can be present within the encapsulation formed by the cover parts 77, 82, which, for instance, can correspond to the exemplary embodiments according to FIGS. 13 to 24.

While various embodiments have been chosen to illustrate the invention, it will be understood by those skilled in the art that various changes and modifications can be made therein without departing from the scope of the invention as defined in the claims.

The invention claimed is:

1. A dispensing device, comprising:
   a container having a receiving space containing a dispensable medium; and
   a dispensing element coupled to said container and capable of extracting said dispensable medium from said container, said dispensing element include a control body being coupled to a connecting body and being rotatable relative to said connecting body, said connecting body being guided for longitudinal movement in a housing part of said dispensing element from an inactive initial position into an active extraction position in which said receiving space and said dispensing element are in fluid communication, said control body having a first control part being abutable with a sloped control path of said connecting body, said control body being rotatable in two-opposite directions without moving in an axial direction relative to said housing part with said first control part moving said connecting body from the inactive initial position to the active extraction position by engagement of said control part and said sloped control path.

2. A dispensing device according to claim 1 wherein said control body comprises a second control part diametrically opposite said first control part relative to a longitudinal axis of the dispensing device, said first and second control parts being rotatable relative to said connecting body from lower vertex positions on said sloped control path in the inactive initial position to upper vertex positions being above said lower vertex positions in an axial direction relative to said longitudinal axis.

3. A dispensing device according to claim 1 wherein said sloped control path is on a hollow ring and coaxially encompasses a connecting channel of said connecting body; and
   a functional body on said connecting body for dispensing said dispensable medium from the dispensing device.

4. A dispensing device according to claim 3 wherein said functional body comprises at least one of a cannula, a hollow mandrel, a dropper, an ointment or gel applicator, a nozzle, a connecting part, a conical connection, or a closure part.

5. A dispensing device according to claim 3 wherein said functional body is integral with said connecting body.

6. A dispensing device according to claim 3 wherein said control body is a protective cover being over said functional body and supporting on an inside thereof said control part, said control part comprising an inwardly projecting lug part having an at least partially convex surface in a direction of said sloped control path of said connecting body when said protective cover is on the dispensing device.

7. A dispensing device according to claim 1 wherein said control body comprises a protruding annular segment in a direction of an open end of said control body, said protruding annular segment under an annular segment on said housing part in the inactive initial position of said control body; and
   after a rotation of said control body around a predetermined distance moving said connecting body into the active extraction position, said protruding annular segment of said control body being disengaged from said protruding annular segment on said housing part allowing removal of said control body from said housing part.

8. A dispensing device according to claim 1 wherein said connecting body comprises a longitudinal guide engaging said housing part, permitting said connecting body to move longitudinally in said housing part and securing said connecting body against rotation relative to said housing part.

9. A dispensing device according to claim 1 wherein said container is one of molded to said housing part or sequentially connected to said housing part as an independent component.

10. A carrier unit for a functional body, the carrier unit comprising:
    a housing part;
    a connecting body guided for longitudinal movement in said housing part from an inactive initial position into an active extraction position; and
    a control body coupled to said connecting body and being rotatable relative to said connecting body, said control body having a control part abuttable with a sloped control path on said connecting body, said control body with said control part being rotatable in two opposite directions relative to said housing part without axial movement moving said connecting body from the inactive initial position to the active extraction position in a longitudinal direction of said connecting body as said control part moves along said sloped control path.

11. A container system, comprising:
    a container having a receiving space containing a dispensable medium; and
    a dispensing element coupled to said container and capable of extracting said dispensable medium from said container, said dispensing element include a control body being coupled to a connecting body and being rotatable relative to said connecting body, said connecting body being guided for longitudinal movement in a housing part of said dispensing element from an inactive initial position into an active extraction position in which said receiving space and said dispensing element are in fluid communication, said control body having a first control part being abutable with a sloped control path of said connecting body, said control body being rotatable in two-opposite directions without moving in an axial direction relative to said housing part with said first control part moving said connecting body from the inactive initial position to the active extraction position by engagement of said control part and said sloped control path;
    a functional body on said connecting body for dispensing said dispensable medium, said functional body by being covered by said control body; and
    an outer sheath extending over said control body and said housing part and having sheath parts separable from one another along a separation point to expose said control body and said housing part.

12. A dispensing device according to claim 1 wherein said sloped control path comprises first and second sloped sections that are mirror images of one another.

13. A carrier unit according to claim 10 wherein said sloped control path comprises first and second sloped sections that are mirror images of one another.

14. A container unit according to claim 11 wherein said sloped control path comprises first and second sloped sections that are mirror images of one another.

\* \* \* \* \*